United States Patent
Demos et al.

(10) Patent No.: US 10,390,709 B2
(45) Date of Patent: Aug. 27, 2019

(54) NON-CONTACT OPTICAL SYSTEM FOR DETECTING ULTRASOUND WAVES FROM A SURFACE

(75) Inventors: Stavros G. Demos, Livermore, CA (US); Alexander M. Rubenchik, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 334 days.

(21) Appl. No.: 13/983,736

(22) PCT Filed: Mar. 13, 2012

(86) PCT No.: PCT/US2012/028944
§ 371 (c)(1),
(2), (4) Date: Sep. 3, 2013

(87) PCT Pub. No.: WO2012/125649
PCT Pub. Date: Sep. 20, 2012

(65) Prior Publication Data
US 2013/0338504 A1      Dec. 19, 2013

Related U.S. Application Data

(60) Provisional application No. 61/452,506, filed on Mar. 14, 2011.

(51) Int. Cl.
*A61B 5/00* (2006.01)
*A61B 8/00* (2006.01)

(52) U.S. Cl.
CPC .......... *A61B 5/0097* (2013.01); *A61B 8/4272* (2013.01); *A61B 8/4281* (2013.01)

(58) Field of Classification Search
CPC ... A61B 8/4281; A61B 5/0095; A61B 5/0097; A61B 5/4271; A61B 5/4281; G01N 21/1702
See application file for complete search history.

(56) References Cited

U.S. PATENT DOCUMENTS

| 5,080,491 A | * | 1/1992 | Monchalin | G01D 5/266 356/493 |
| 5,379,769 A | | 1/1995 | Matsudo et al. | |

(Continued)

OTHER PUBLICATIONS

Monchalin, "Optical Detection of Ultrasound at a Distance Using a Confocal Fabry-Perot Interferometer," Jul. 1, 1985, Apple. Phys. Lett., 47 (1), pp. 14-16.*

(Continued)

*Primary Examiner* — Boniface N Nganga
(74) *Attorney, Agent, or Firm* — Eddie E. Scott

(57) ABSTRACT

A system for detecting pressure, acoustic or ultrasound waves within an entity having a surface including the steps of attaching a signal converting material to the surface. The waves are generated by direct ejection from the surface, generation via energy deposition on the surface, generated spontaneously or, generated by directing light energy to the light absorbing target. The absorbing target subsequently generates acoustic pressure waves. The acoustic waves propagate to the surface of the entity and the signal converting material, wherein the acoustic pressure waves create vibrations in the signal converting material; and detecting the waves in the signal converting material with an optical detection system. Information about the absorbing target is obtained by the absorbing target reflecting the waves. The signal converting material can be a gel-like material containing optical elements, a multi-layer patch, or other material.

4 Claims, 14 Drawing Sheets

(56) References Cited

U.S. PATENT DOCUMENTS

| | | | |
|---|---|---|---|
| 5,485,842 A | | 1/1996 | Quistgaard |
| 5,529,070 A | | 6/1996 | Augustine et al. |
| 5,615,675 A | * | 4/1997 | O'Donnell et al. .......... 600/425 |
| 5,806,521 A | | 9/1998 | Morimoto et al. |
| 5,840,023 A | * | 11/1998 | Oraevsky et al. ............ 600/407 |
| 6,139,499 A | | 10/2000 | Wilk |
| 2006/0198760 A1 | | 9/2006 | Potyrailo et al. |
| 2006/0272419 A1 | | 12/2006 | Maris et al. |
| 2012/0200845 A1 | * | 8/2012 | Rousseau ........... G01N 21/1702 356/72 |
| 2016/0113507 A1 | * | 4/2016 | Reza .................. G01N 21/1717 356/477 |
| 2016/0128578 A1 | * | 5/2016 | Demos ................. A61B 5/4064 600/407 |

OTHER PUBLICATIONS

Zhu, "Optimization of Matching Layer Design for Medical Ultrasonic Transducer," Aug. 2008, The Pennsylvania State University, pp. 4-5 and 33-81.*

Rousseau et al., "Non-contact photoacoustic tomography and ultrasonography for tissue imaging," Biomedical Optics Express, 3 (1), 16-25 (2011).

* cited by examiner

NON-CONTACT OPTICAL SYSTEM FOR DETECTING ULTRASOUND WAVES FROM A SURFACE

CROSS-REFERENCE TO RELATED APPLICATIONS

The present application claims benefit under 35 U.S.C. § 119(e) of U.S. Provisional Patent Application No. 61/452,506 filed Mar. 14, 2011 entitled "Signal conduit medium for non-contact registration of pressure, sound and ultrasound waves with light-based methods," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to non-contact registration of pressure, sound and ultrasound waves and more particularly to a non-contact, all optical system for detecting ultrasound or other types of pressure waves.

State of Technology

Ultrasound is widely used in various applications such as in the medical field and for the detection of defects in solid-state material or components. Typically, the ultrasound waves are injected in to the material and the reflected signal from an object (such as a crack in a homogeneous material or a cyst or tumor in a tissue or organ system) is detected and/or imaged using an appropriate ultrasound detector system. Typically, an impedance matching material is used to effectively couple the ultrasound wave energy from the emitter to the material and the reflected signal from the material to the detector for minimizing loss of signal.

The ultrasound signal to be detected can also be generated via other means. In this case, the object of interest becomes the primary emitter of the ultrasound signal. One such example is associated by the absorption of another form of energy by a defect or defective region which in turn leads to localized energy deposition followed by heating, spatial expansion and subsequently the emission of a pressure wave by this defect. When this process is modulated at ultrasound frequencies, the repeated production of pressure waves leads to the generation of the ultrasound waves that originate in the defect location.

Another method suitable for biomedical applications is associated with the injection of light pulses that is absorbed by structures of interest such as cysts, tumors and normal or abnormal blood concentrations. The resulting pressure waves following the absorption of light energy can then be used to achieve detection or imaging of the tissue structure of interest. Contrary to the highly diffusive way the light propagates in tissues, ultrasound waves exhibit comparatively very limited attenuation and thus, is capable for transporting the signal information through greater distances inside the tissue.

Ultrasound waves are typically strongly reflected by a surface or object that presents impedance mismatching (such as the skin-air interface or at the surface of a solid state material). For this reason, an impedance matching fluid is typically used to achieve best coupling of the ultrasound wave energy to the detection system. This limits the use of ultrasound methods to detection schemes that require the detector to be in contact with the system under examination (such as the tissue).

The present invention provides a medium that when applied on the surface of an object, such as tissue, allows for remote detection and registration of the ultrasound waves reaching the surface using light-based methods. The method is also suitable for detecting of pressure waves outside the ultrasound frequency range, thus it can be used to detect sound waves or any type of pressure waves that can be transmitted through the tissue or other material of interest.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an all-optical system suitable for the detection of ultrasound waves reaching the surface of a material such as a solid state material or tissue. The system is based on the conversion of the vibrational signal carried by the pressure, acoustic or ultrasound wave into an optical signal via the use of a specially designed impedance matching signal converting material (IMSCM) that is applied on the surface. This optical signal can be obtained from the modulation of one or more optical properties of the IMSCM in response to exposure to the ultrasound waves, thus offering a method to convert the ultrasound signal to an optical signal. The optical signal can then be captured using an appropriate detection system and can be employed without need to be in contact with the surface. The present invention has use in medical applications, material inspection applications, and other applications involving detection systems that can be employed without being in contact with the surface.

The invention is susceptible to modifications and alternative forms. The terms "pressure wave," "pressure waves," "acoustic wave," "acoustic waves," "ultrasound wave," "ultrasound waves," "sound wave," and "sound waves" are used in this application. There terms can be used interchangeably and in general are considered pressure waves.

Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
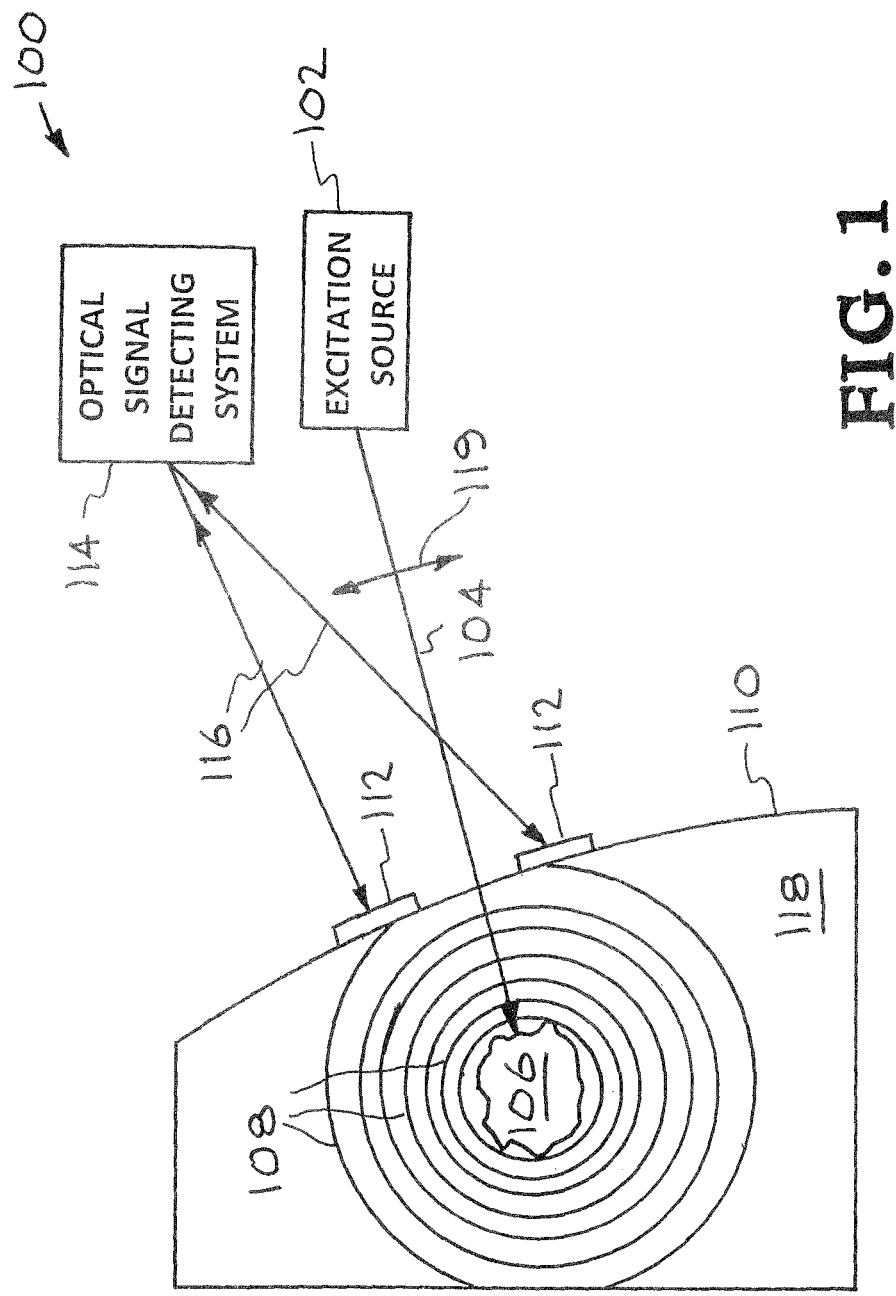
FIG. 1 illustrates a non-contact, all optical system for detecting ultrasound.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a non-contact, all optical system to detect ultrasound. Light is used to illuminate the material where ultrasound waves are propagating and reach its surface. The illumination can be delivered in various arrangements, using point illumination, small area illumination, multi point illumination, multi-area illumination or large field illumination or various combinations of the above.

Some of the advantages of the present invention utilizing IMSCM (gels or other type of material with similar properties) in which an appropriate ensemble of particles having a suitable size, shape and material composition to detect the arrival of pressure waves on a surface using light based methods include the following advantages: (1) The present invention will exhibit strong reflected signal from a locally flat surface. (2) The ultrasound driven surface oscillation can be easily detected via means well established in the scientific literature (such as interference). (3) One laser can be used for the detection of the signal arriving at multiple detection points using the same processing unit. (4) TA holographic scheme with imaging of ultrasound pattern is possible. (5) The method can provide extremely high sensitivity. (6) It can detect pressure waves generated by an external energy source (such as a laser source depositing energy in various tissue locations) (7) It can detect pressure waves generated by normal body functions (such as heart beat and blood flow) (8) It can detect and monitor pressure waves generated by abnormal conditions (such as from blood flow though a vascular stenosis or an aneurysm) (9) It can be used for monitoring complex medical conditions with a single modality such as following a traumatic injury (such a head injury) to monitor blood volume, oxygenation, flow and response as a function of time or due to therapy or surgical intervention.

This interaction of the microscopic optical elements with the ultrasound waves is then used to convert the ultrasound signal into an optical signal. Specifically, the microscopic optical elements can be designed to cause maximum modulation of the illumination light that is scattered by them (scattering of the illumination light) leading to changes in the scattered wave front, or scattering intensity or scattering spectrum. They can also be designed to cause maximum change in the speckle patterns in the presence of the ultrasound signal and as a function of its intensity. These microscopic optical elements can also be equipped with florescence capabilities while their interaction with the ultrasound waves can be monitored by the change in the fluorescence intensity or fluorescence frequency or emission spectrum.

Other properties of the light can be used as reporters of the interaction of the microscopic optical elements with the ultrasound waves such as change in the polarization, phase, coherence etc. of the scattered or emitted light. Employment of this method in various applications may demonstrate that a different optical property may be more suitable for monitoring different systems.

The optical map of the ultrasound wave intensity or energy within the material can then be used to detect the source or sources of the signal as well as their spatial distribution in three dimensions and their physical characteristics. As a result, a reconstruction of the structures of interest can be achieved using methods similar to those already in existence.

The use of this specially designed impedance matching signal converting material (IMSCM) containing the microscopic optical elements to report the presence and intensity of ultrasound waves will allow the application of ultrasound detection and imaging using a noncontact mode. This may be particularly important in various applications where the need for detection of the ultrasound signal using a detector in contact with the surface is not possible. It may also be used as a method to increase the sensitivity for the detection of ultrasound signals that are otherwise not detectable using in contact ultrasound detector schemes.

The present invention provides a non-contact, all optical method to detect ultrasound or other types of pressure waves. The detected pressure waves can be generated by three or more different methods briefly described As follows:

Method 1—A form of energy, such as electromagnetic waves, microwaves, or acoustic waves, is directed to an energy absorbing target to generate the ultrasound signal via absorption of the form of energy and subsequent energy relaxation with localized temperature increase which in turn will generate the pressure waves. This form of energy can be light that can be produced by a laser or a non-laser source such as an incandescent source, a fluorescent-low pressure discharge lamp, a high-intensity or pressure discharge lamp, a flashlamp, or arc lamp, or light-emitting diode or other non-laser source.

Method 2—The pressure waves are naturally created by the body as a result of normal function or in response to or as a result of an abnormal condition.

Method 3—The pressure waves are injected in the material thought the surface either via a devise in contact with the surface or as a result of the presence of an energy source delivering energy on the surface or a combination of the suitable material and energy source.

In various medical applications, ultra-sound carry out diagnostic information such as about possible tumors and their location and structure. In various nondestructive testing applications, ultra-sound is used to obtain diagnostic information such as information about possible cracks or defects in a material. For example, the present invention can be used for the detection of cracks in airplane components.

In one embodiment the present invention uses a laser to generate the ultrasound signal inside a material. This ultrasound signal will propagate and reach the surface of the material which in response will vibrate. These surface vibrations can be measured in multiple points via optical methods which can monitor the vibrational motion of the surface. Interferometry is one of such methods and has been used to detect the vibration of the surface of various materials, typically solid state materials with polished surfaces. However, in many materials and in particular in tissues, it is difficult to rely directly on light reflection measurements to the surface in order to detect the pressure waves arriving on the surface for the following reasons: (1) Light reflection is diffusive and the signals from different points interfere to effectively generate a strong background noise; (2) The tissue surface is unpredictably not-flat degrading the signal information; (3) The hydration of the tissue related to the medical condition, stress, environment etc. (or other liquid substance) affects its reflectivity limiting signal quantification.

The present invention provides a new approach that addresses these difficulties.

In one embodiment, applicants apply on the skin the impedance matching signal converting material (IMSCM), such as a gel or cream, which matches the skin impedance for ultrasound transmission and to add to gel the small high reflective metal particles with size smaller then interrogating laser wavelength. The ultrasound waves from tissue will freely propagates to the IMSCM (gel) surface causing a corresponding spatial displacement. If the distance between the particles is smaller or about the same with the interrogating laser wavelength the light will be reflected like from the uniform reflective material (such as a mirror). The surface tension makes the surface locally flat and diffused light scattering component will be suppressed or eliminated.

It is possible to show that the addition of small volume fraction of small particles almost doesn't change the gel impedance and the standard ultrasound imaging gel can be used.

When the particle size in the gel is much smaller then light wavelength their specific shape is not important. However, one can consider particles with sizes comparable or larger than the light wavelength. In this case, the shape of the particles can affect the way these particles interact with the ultrasound (or other type of pressure waves) and the light. The results of such complex for specific special shape or size of the particle can be beneficial for the detection and registration of the pressure waves within the teachings of this method. Specifically: (1) For particles larger than the laser wavelength the reflection will be produced by the individual particles. If one can discriminate between the different particles the diagnostic spatial resolution can be improved. (2) Optimizing the particles shape, using rods, balls, plated etc. one can enhance the ultrasound interaction with the particles and to improve the ability to detect weak pressure or ultrasound signals. (3) The effect of surface tension can produce the regular array for particles of specific shape e.g. rods. This regular structure can be used for the signal sensitivity improvements. The regular structure reflection for different polarization will provide the information on ultra-sound wave polarizations, enhancing the diagnostic capacity The present invention utilizes a specially designed impedance matching signal converting material (IMSCM) to convert the ultrasound signal reaching the surface of the material into an optical signal. For example, in one embodiment the present invention utilizes a cream-type material that is applied on the surface of the object under examination (such as tissue). This cream-type material is designed to offer two functions. The first is to provide impedance matching with the substrate material (such as tissue) so that the ultrasound waves can effectively propagate into this material. The second function is that the ultrasound waves can interact with the custom optical elements of microscopic size that are embedded in this cream-type material in a fashion that enables conversion of the acoustic signal to an optical signal such as modulation of the optical intensity, phase, polarization, complex index of refraction or other type of optical signal or property. These optical elements can be embedded in any type of material that offers impedance matching (such as the materials currently used in conventional ultrasound imaging) but can also support the interaction of the microscopic optical elements with the ultrasound waves.

The method can also be used to detect objects or structures that reflect the pressure, acoustic or ultrasound waves in a fashion similar to that employed in conventional ultrasound imaging/detection technology. In conventional ultrasound, the pressure waves are injected from the surface and the reflected signal of various internal structures is detected. Within the teaching of this invention, the sound waves can be injected in to the material using a piezoelectric transducer in contact with the surface and the reflected signal can be detected in one or multiple locations using the noncontact method described herein. Receiving the reflected signal in multiple locations can enhance the sensitivity and/or volume of information obtained in certain applications resulting for example to better image resolution and larger imaging depth.

In another embodiment, the pressure waves can be generated on the surface by an energy source depositing energy on the surface that causes the generation of the pressure waves. This can be for example a microwave or optical source that is absorbed by the surface to generate the pressure wave as part of the energy relaxation process. A specially designed material can also be applied on certain locations on the surface and subsequently excited by an external energy source such as a light source to generate the pressure waves. The later method is also a noncontact method but utilizes an external medium to generate the pressure waves on the surface.

Referring now to the drawings and in particular to FIG. 1, a system that illustrates a non-contact, all optical system to detect ultrasound is shown. The system is designated generally by the reference numeral 100. The system 100 provides an all-optical approach and system arrangement suitable for the detection of ultrasound waves reaching the surface of a material such as a solid-state material or tissue. The system is based on the conversion of the vibrational motion carried by an ultrasound wave into an optical signal via the use of a specially designed impedance matching signal converting material (IMSCM) that is applied on the surface. This optical signal can be obtained from the modulation of the light scattered by optical elements embedded in the IMSCM that are also sensitive to the ultrasound signals or the structure of the IMSCM is changing in response to the vibrations induced by the ultrasound signals, thus offering a system for converting the ultrasound signal to an optical signal. The optical signal can then be captured using an appropriate detection system and can be employed without need to be in contact with the surface.

As illustrated in FIG. 1, the system 100 employs an excitation energy source such as a microwave source or a light source. The energy source can operate at one or more frequencies 104 from an excitation energy source 102 (such as a laser) used to deposit energy on a energy (such as light) absorbing target object of interest 106 which subsequently generates acoustic pressure waves 108 that propagate to the surface 110. One or more locations on the surface 110 are covered by an IMSCM 112 (for example, a reflective gel containing particles) that is used to detect the arriving pressure (acoustic) waves 108 using an optical ultrasound detection system 114.

The IMSCM (for example, a reflective gel containing particles) 112 has optical elements suspended in the reflective gel-like medium. The optical elements can be microscopic particles. In one or more embodiments the optical elements suspended in the reflective gel-like medium are nanoparticles. In one or more embodiments the optical elements suspended in the reflective gel-like medium are particles of reflective materials. In one or more embodiments the optical elements suspended in the reflective gel-like medium are aluminum particles. In one or more embodiments the optical elements suspended in the reflective gel-like medium are silver particles. In one or more embodiments the optical elements suspended in the reflective gel-like medium are gold particles. In one or more embodiments the optical elements suspended in the reflective gel-like medium are particles of refractive materials e.g. high index of refraction materials or birefringent materials, or fluorescing materials, or materials which change the polarization of light or can alter some other property of incoming light (interacting with it) suspended in the gel so that when the gel is applied to the subject medium the spatial arrangement (e.g. position, displacement, orientation, group organization, etc) and/or physical property and/or optical property of the optical elements are changed by a pressure wave (e.g. sound or ultrasound waves) from the subject medium which in turn produces a corresponding change in the optical response of the composition to an interrogating light (e.g. laser or LED source operating at a suitable single or multiple wavelengths).

The IMSCM 112 maybe have a specially designed structure such as a multilayer structure. Such multilayer structure can be a plastic material containing layers of material with differing index of refraction. As the arriving pressure waves cause the vibration of the surface and the IMSCM multilayer structure, the thickness of the layers can be modified. This in turn will cause a change in the interaction of the IMSCM with the incoming light interacting with it which can be used to detect the presence and strength of the surface pressure waves. For example, the spectrum of the scattered light under broadband illumination or the intensity of the scattered light at a selected monochromatic illumination will be modulated by the arriving pressure waves.

Preliminary research and computational studies supporting the modeling of the reflective gel properties were conducted by Applicants. In the following Applicants summarize some theoretical considerations in support of this study. The optically reflective gel to enable conversion of the ultrasound signal from the tissue to an optical signal must not cause any reflection of the acoustic signal on the tissue-gel interface. The reflection coefficient for the acoustic wave can be written as:

$$R = \frac{Z_g - Z}{Z + Z_g}; Z = \rho s \qquad \text{[Equation 1]}$$

where index g is related to the gel. The acoustic impedance is the product of the material density ($\rho$) and the sound speed in the material (s). To eliminate any acoustic reflection, we must match the impedance of the tissue (Z) and gel ($Z_g$). The gel materials currently used in US imaging systems are designed to provide such impedance match. But the addition of metal particles can change the gel impedance.

Since the particles are smaller than the acoustic wavelength, the sound waves will propagate in the gel material (which has a fixed mass ratio for gel and nanoparticles) as in a homogeneous medium having an effective sound speed ($s_t$) and acoustic impedance ($Z_t$). Let us define the mass fraction of the metal nanoparticle material as x. The Gibbs function (G) of the system (Gibbs free energy) will be the sum of the Gibbs function of the two components. The specific volume (V) of the system is derived by differentiation of the Gibbs function by the pressure:

$$V = \frac{\partial G}{\partial P} = xV_1 + (1-x)V_2 \qquad \text{[Equation 2]}$$

where indices 1 and 2 related to the nanoparticle and gel materials, respectively. The differentiation of the V by pressure provides the expression the allows to calculate the sound speed of the mixture ($s_t$) as following:

$$\frac{dV}{dP} = -\frac{V^2}{s_t^2} = x\frac{dV_1}{dP} + (1-x)\frac{dV_2}{dP} = -\left(x\frac{V_1^2}{s_1^2} + (1-x)\frac{V_2^2}{s_2^2}\right) \qquad \text{[Equation 3]}$$

Using eq. 2, the sound speed ($s_t$) is given:

$$s_t^2 = \frac{V^2}{\frac{x}{\rho_1^2 s_1^2} + \frac{1-x}{\rho_2^2 s_2^2}} \quad \text{[Equation 4]}$$

Consequently, the acoustic impedance ($Z_t$) of the composite material is:

$$Z_t^2 = \frac{(Z_1 Z_2)^2}{xZ_2^2 + Z_1^2(1-x)} \approx \frac{Z_2^2}{(1-x)}; Z_1^2 >> Z_2^2 \quad \text{[Equation 5]}$$

Assuming the nanoparticles have a diameter of 5 nm and the average separation between nanoparticles is 100 nm, the estimated mass fraction of metal nanoparticle (x) will be on the order of $10^{-3}$ and based on the above theoretical considerations, the acoustic impedance of the gel ($Z_t$) will change by less than 0.1%. This result indicates that by adding nanoparticles in the gel material designed for current generation US imaging system will provide a gel material that offers the required acoustic impedance and optical reflectivity for Applicants' proposed design.

Figure 2:
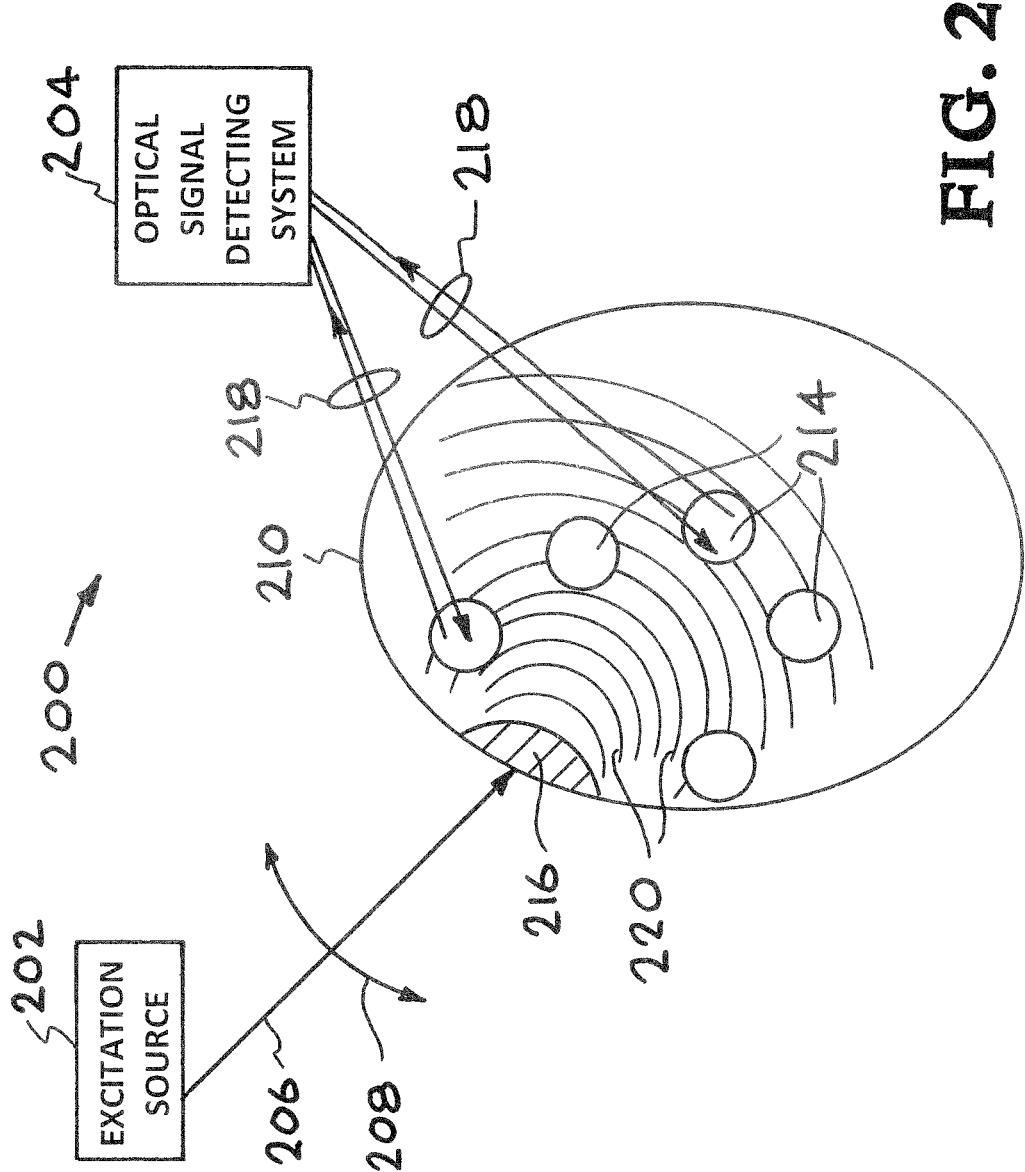
FIG. 2 illustrates a non-contact, all optical system for detecting ultrasound and obtaining information regarding a possible head injury or condition.

Referring to FIG. 2 a non-contact, all optical system for detecting ultrasound and obtaining information regarding a possible head injury or condition is shown. FIG. 2 is a simplified representation of a patient's head 210 that has suffered a head injury and possible internal head injury resulting, for example, in a hematoma 216. The system illustrated in FIG. 2 is designated generally by the reference numeral 200. The excitation source 202 can be used to scan the beam 206 and determine information such as the location of the hematoma 216. The scanning is illustrated by the arrow 208. Alternatively, the location of the hematoma 216 may be know using a different modality and the excitation source 202 is fixed on this location to monitor changes with time. The excitation source 202 may involve one or more wavelengths so that functional information about the target region 212 can be obtained. For example, the excitation source 202 can contain wavelengths that can help assess the content of the hematoma in oxyhemoglobin, deoxyhemoglobin and methemoglobin. The amount of absorption at each wavelength will be directly related to the strength of the pressure waves 220 generated. In turn, this will lead to a corresponding modulation of the signal recorded by the optical signal capturing system. This strength can be deconvoluted in to functional information using already established methods.

One or more locations 214 on the surface are covered by the IMSCM 214 that is used to detect the arriving pressure (acoustic) waves 220 using an optical ultrasound detection system 214. The IMSCM 214 provide conversion of the acoustic signal 220 into optical signal 218. For example, the IMSCM can be a reflective gel containing metal nanoparticles at sufficiently high concentration so that it behaves as a perfect reflector.

The optical ultrasound detection system 214 detects the arriving waves 220 using the optical signal 218. The ultrasound waves 220 from the tissue freely propagate to the IMSCM 214 surface causing a corresponding change ion the optical signal. For example, the spatial displacement of the gel 214 surface can be detected with interferometric methods. Detection of the spatial displacement of the gel 214 surface by the optical signal 218 at one or more location 214 enables increased sensitivity and volume of information.

Referring now to FIGS. 3A, 3B, 3C and 3D; embodiments of the signal converting material (SCM) 320 containing optical elements 324 that allow the conversion of the acoustic signal into an optical signal are shown. The signal converting material is designated by the reference numeral 320 in each of the embodiments illustrated in FIGS. 3A, 3B, 3C and 3D. The signal converting material can be a gel, a cream, a patch, or other substance containing the optical elements 324.

Figure 3A:
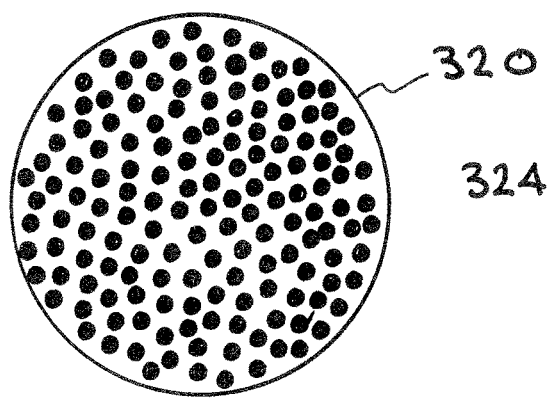
FIGS. 3A, 3B, 3C, and 3D show various embodiments of signal converting material that can be used in the non-contact, all optical system for detecting ultrasound of the present invention.

FIG. 3A is an illustration of an embodiment of a signal converting material 320 containing particles 324. The particles 324 can be microscopic particles. The particles 324 are suspended in the reflective gel-like medium of the signal converting material 220. In one or more embodiments the particles 324 suspended in a gel-like medium are particles of reflective materials. In one or more embodiments the particles 324 suspended in the gel-like medium are aluminum particles. In one or more embodiments the particles 324 suspended in the gel-like medium are silver particles. In one or more embodiments the particles 324 suspended in the gel-like medium are gold particles. In one or more embodiments the particles 324 suspended in the gel-like medium are nanoparticles. In one or more embodiments the particles 324 suspended in the gel-like medium are metal particles.

In one or more embodiments the particles 324 suspended in the gel-like medium are particles of refractive materials e.g. high index of refraction materials or birefringent materials, or fluorescing materials, or materials which change the polarization of light or can alter some other property of incoming light interacting with it) suspended in the gel so that when the gel is applied to the subject medium the spatial arrangement (e.g. position, displacement, orientation, group organization, etc) and/or physical property and/or optical property of the optical elements are changed by a pressure wave (e.g. sound or ultrasound waves) from the subject medium which in turn produces a corresponding change in the optical response of the composition to an interrogating light (e.g. laser or LED source operating at a suitable single or multiple wavelengths). In one embodiment, these optical elements are metal nanoparticles at sufficiently high concentration so that the converting material behaves as a perfect reflector. In another embodiment, these particles are specially shaped to enable to aforementioned conversion. Yet in another embodiment, these particles have distinct optical properties or their optical properties change as a function of the intensity of the pressure wave strength to enable to aforementioned conversion.

In another embodiment, the signal converting material 322 is a multilayer structure containing layers of material with differing index of refraction. As the arriving pressure waves cause the vibration of the surface and the SCM multilayer structure, the thickness of the layers can be modified. This in turn will cause a change in the interaction of the SCM with the incoming light which can be used to detect the presence and strength of the surface pressure waves. For example, the spectrum of the scattered light under broadband illumination or the intensity of the scattered light at a selected monochromatic illumination will be modulated by the arriving pressure waves.

Figure 3B:
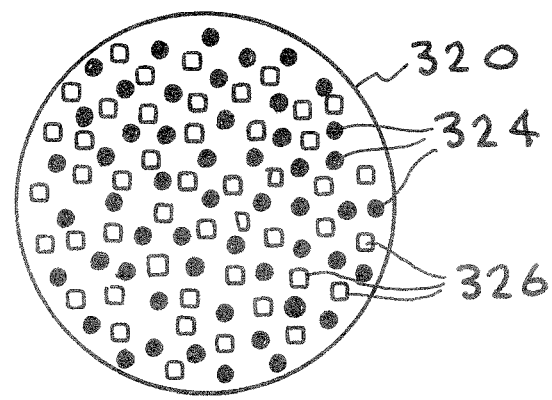

FIG. 3B is an illustration of another embodiment of the signal converting material 322 that contains two or more different types of particles such as particles 324 and larger refractive particles 326. Such arrangement is suitable to achieve a combination of optical properties for signal conversion such as for example the converting material has reflective and diffusive properties or the signal conversion can be achieved by monitoring two or more light properties such as phase, coherence, frequency, intensity etc.

Figure 3C:
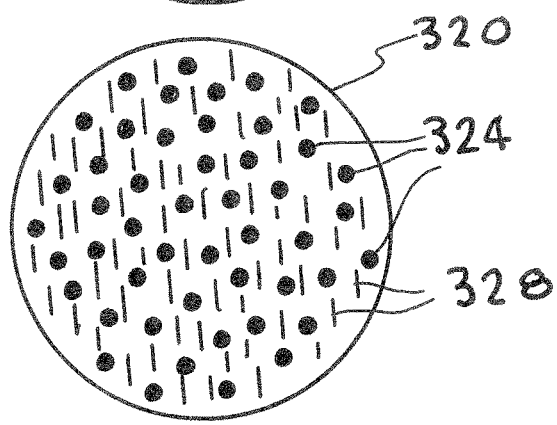

FIG. 3C is an illustration of another embodiment of the signal converting material 322 that contains particles 324 and rods 328. Such arrangement is suitable to achieve a combination of optical properties for signal conversion.

Figure 3D:
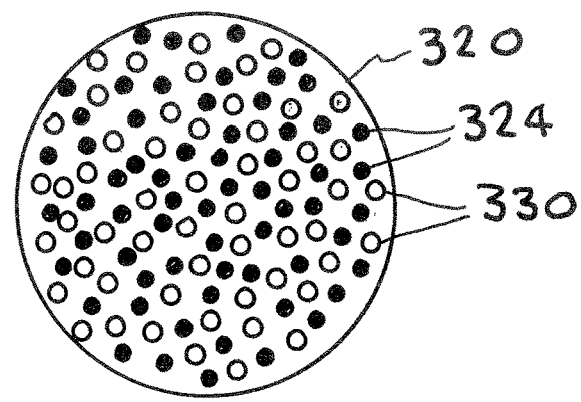

FIG. 3D is an illustration of another embodiment of the signal converting material 322 that contains two or more different types of particles such as particles 324 and larger particles 330 or particles having different properties. Such arrangement is suitable to achieve a combination of optical properties for signal conversion.

Figure 4:
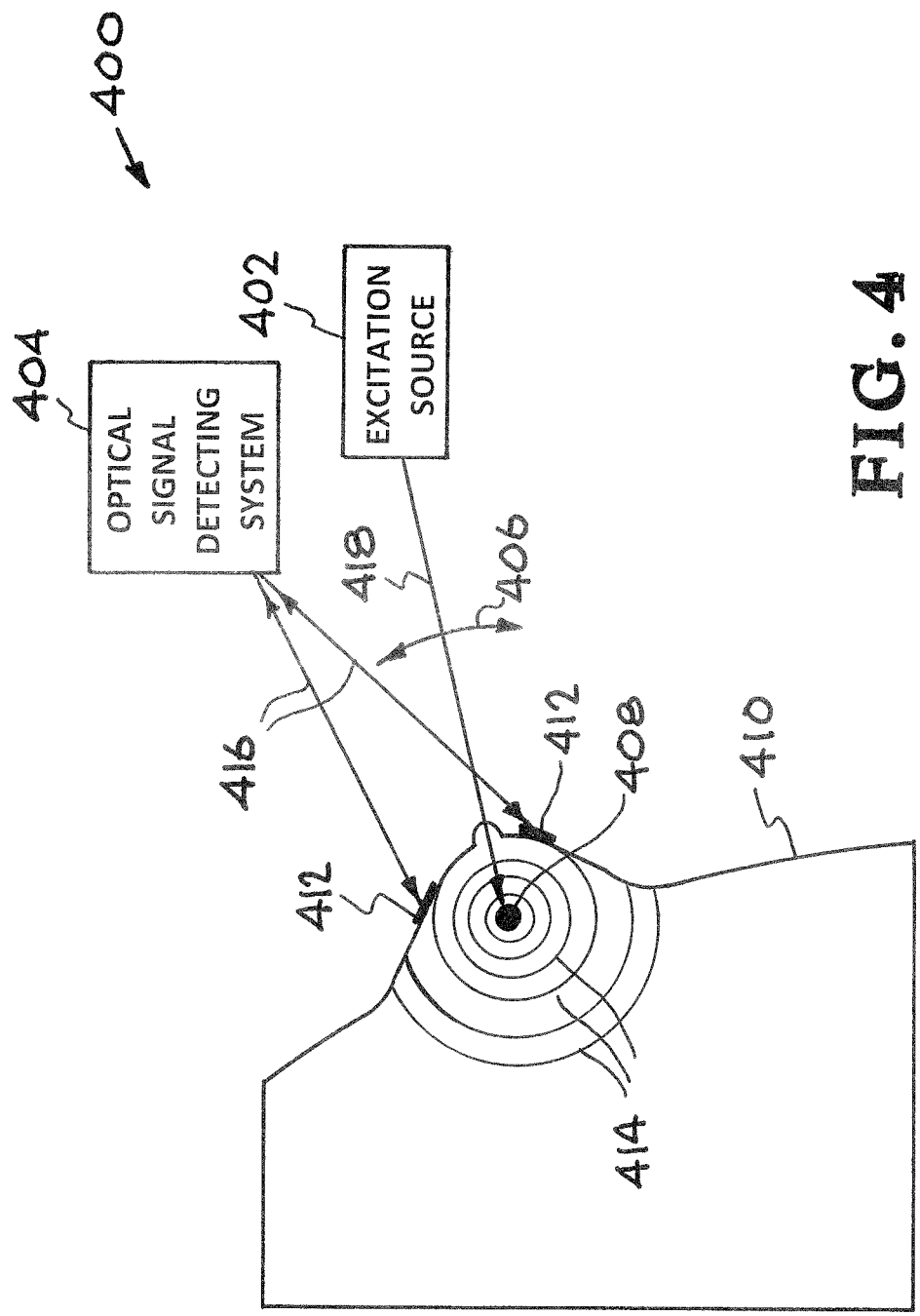
FIG. 4 illustrates a non-contact, all optical system for detecting ultrasound and obtaining information regarding possible breast tumors and cysts.

Referring now to FIG. 4, a non-contact, all optical system for detecting ultrasound and obtaining information regarding possible breast tumors and cysts is shown. The system is designated generally by the reference numeral 400. A tumor 408 is being detected by the system 400. The tumor 408 is known to cause local structural and functional alterations such as those related to blood volume and oxygenation.

An excitation source 402 with beam 418 is used to scan and locate the location of the tumor 408. Alternatively, the location of tumor 408 maybe known using a different modality and the excitation source 402 is fixed on this location to monitor changes with time and intervention (such as from chemotherapy or other type of treatment). The tumor may also contain extrinsic agent used to enable detection and/or therapy.

The excitation source 402 may involve one or more wavelengths so that structural and/or functional information about the tumor can be obtained. The amount of absorption at each wavelength will be directly related to the strength of the pressure waves generated. In turn, this will lead to a corresponding modulation of the signal recorded by the optical signal capturing system. This strength can be deconvoluted in to functional information using already established methods. Detection of the optical signal at one or more location enables increased sensitivity and volume of information. The excitation source 402 can also be scanned to monitor spatial changes with time as a result to therapeutic intervention or progress of the disease. The converting material 412 is used with the optical detecting system 404 using the signal 416.

Figure 5:
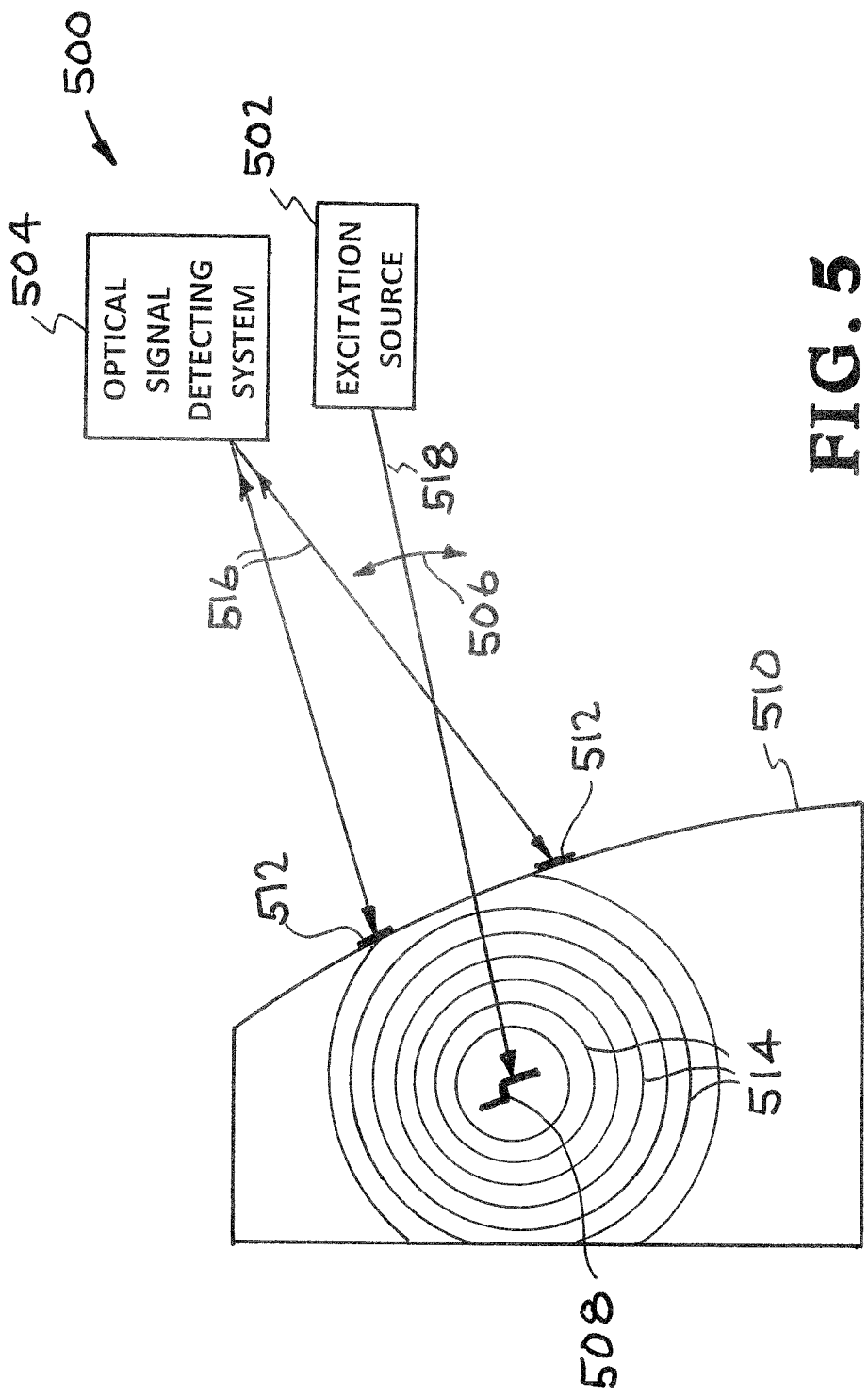
FIG. 5 illustrates a non-contact, all optical system for detecting ultrasound and obtaining information regarding a patient's internal structures, organs, or other internal features.

Referring now to FIG. 5, a non-contact, all optical system for detecting ultrasound and obtaining information regarding a patient's internal organ or structure is shown. The system is designated generally by the reference numeral 500. The system 500 is a non-contact, all optical system to detect ultrasound. The system 500 is a non-contact, all optical system for detecting ultrasound and obtaining information regarding a patient's internal organs, tissue structures or blood vessels. The system 500 employs one or more wavelengths 518 from an excitation laser 502 used to deposit energy on the absorbing target 508 which subsequently generates acoustic pressure waves 514 that propagate to the surface of the tissue 510.

The system 500 is illustrated detecting information about a blood vessel 508 in FIG. 5. The excitation source 502 is used to scan the beam 518 and determine information about the blood vessel 508. The scanning is illustrated by the arrow 506. The excitation source 502 may involve one or more wavelengths so that functional information about the blood vessel 508 can be obtained. One or more locations on the surface are covered by a signal converting material 512 that is used to detect the arriving pressure (acoustic) waves 514 using an optical ultrasound detection system 504, 516. Such arrangement will be suitable for implementation of the teaching of this invention in a human where the condition is related to increased or decreased absorption of light as a single or multiple wavelengths in order to obtain functional and/or anatomic information. The absorbing target 508 in FIG. 5 may be a blood vessel. The excitation source 502 is used to scan the beam 518 and determine information about the blood vessel 508. The scanning is illustrated by the arrow 506. The excitation source 502 may involve one or more wavelengths so that functional information about the blood vessel 508 can be obtained.

One or more locations on the surface are covered by a signal converting material 512 such as a reflective gel or a patch, that is used to detect the arriving pressure (acoustic) waves 514 using the detection system 504. The signal converting material 512 is a signal converting material containing optical elements or specially designed multilayer structure or other form of material structure and composition that provide conversion of the acoustic signal 514 into optical signal 516.

The optical ultrasound detection system 504 detects the arriving waves 514 using the optical signal 516. The ultrasound waves 514 from the absorbing target (such as blood vessel) 508 freely propagate to the signal converting material 512 causing a corresponding spatial displacement of the signal converting material 512. Detection of the spatial displacement of the signal converting material 512 by the optical signal 516 at one or more location enables increased sensitivity and volume of information.

The system 500 employs one or more wavelengths 518 from an excitation laser 502 used to deposit energy on the absorbing target 508 which subsequently generates acoustic pressure waves 514 that propagate to the surface. One or more locations on the surface are covered by a signal converting material 512 that is used to detect the arriving pressure (acoustic) waves 514 using an optical ultrasound detection system 504. Such arrangement illustrates this invention in a human where the condition is related to increased or decreased absorption of light or other source of energy as a single or multiple wavelengths or frequencies in order to obtain functional and/or anatomic information.

Figure 6:
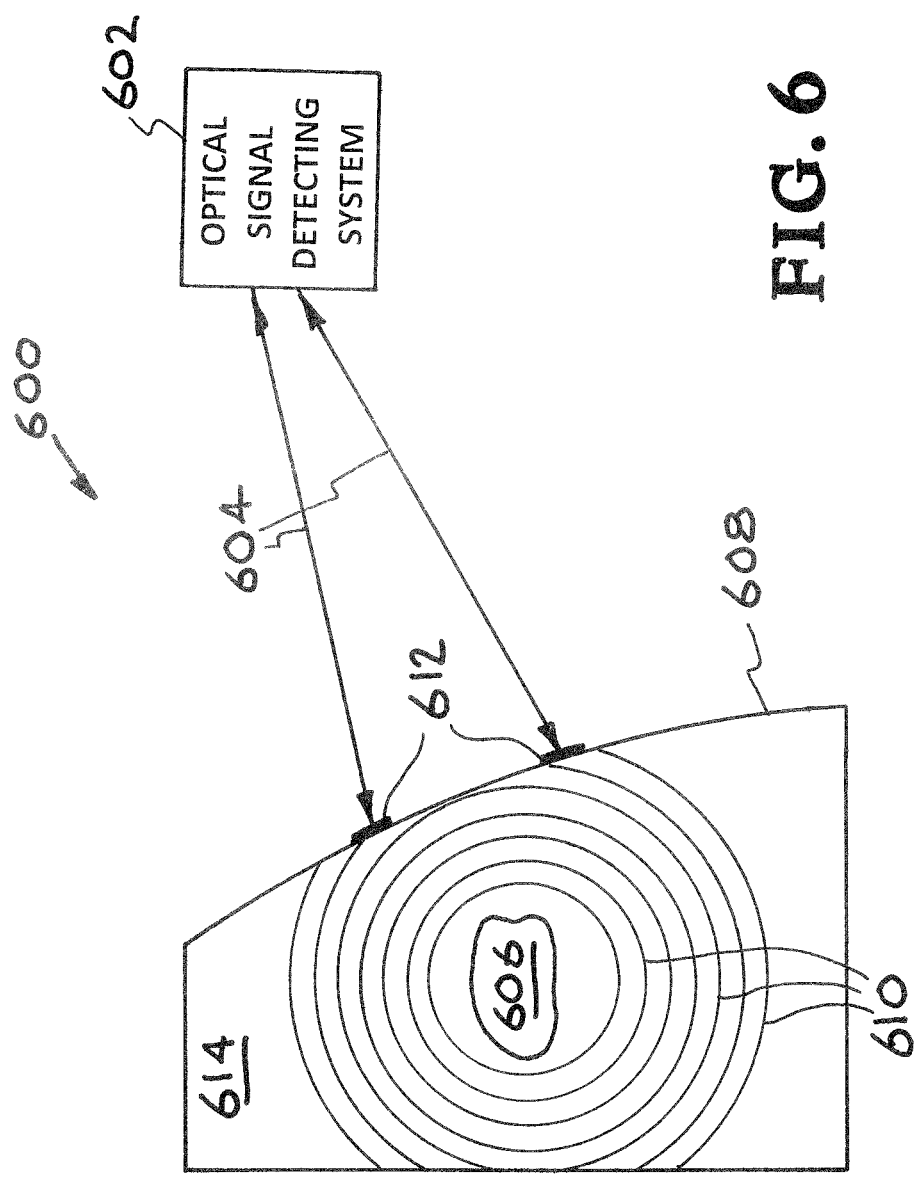
FIG. 6 illustrates a system of the present invention that obtains information using acoustic waves produced within a patient's body.

Referring now to FIG. 6, an embodiment of a system of the present invention is illustrated that relies upon acoustic waves produced within a patient's body. This embodiment of the present invention is designated generally by the reference numeral 600. The system 600 does not include the excitation source used in the previous embodiments.

In certain situations acoustic waves are produced by organs, blood vessels, or features within a patient's body. For example, a blood vessel 606 that has an obstruction will produce acoustic waves 610 within a patient's body. The system 600 remote detection and registration of the ultrasound waves reaching the surface 608 using the optical detecting system 602.

One or more locations on the surface 608 are covered by a signal converting material 612 such as a reflective gel or a patch, that is used to detect the arriving pressure waves 610 using the detection system 602. The signal converting material 612 is a signal converting material containing optical elements that provide conversion of the acoustic signal 610 into optical signal 604.

The optical ultrasound detection system 602 detects the arriving waves 610 using the optical signal 604. The ultrasound waves 610 from the blood vessel 606 propagate to the signal converting material 612 causing a corresponding spatial displacement of the signal converting material 612. Detection of the spatial displacement of the signal converting material 612 by the optical signal 604 at one or more location enables increased sensitivity and volume of information.

Figure 7:
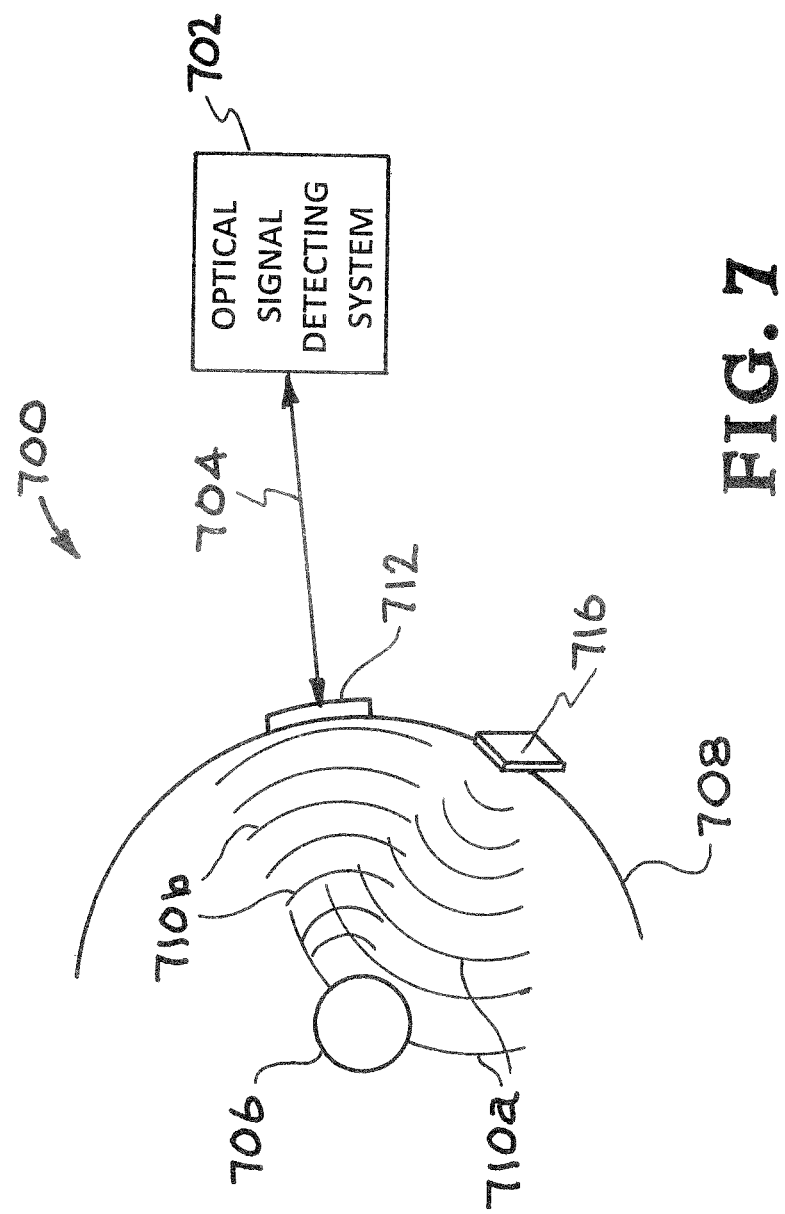
FIG. 7 illustrates a system of the present invention that obtains information using a piezoelectric transducer in contact with the skin's surface.

Referring now to FIG. 7, a non-contact, all optical system for detecting ultrasound is illustrated where the sound waves 710a are injected in to the material using a piezoelectric transducer 716 in contact with the surface 708 and the reflected signal 710b is detected in one or multiple locations using the noncontact system described herein. The system is designated generally by the reference numeral 700. The system 700 provides an all-optical approach and system arrangement suitable for the detection of ultrasound waves 710b reaching the surface 708 of a material such as a solid-state material or tissue. The system 700 is based on the conversion of the vibrational motion carried by an ultrasound wave into an optical signal 704 via the use of a signal converting material (SCM) 712 that is applied on the surface 708. This optical signal 704 can be obtained from the modulation of the light scattered by optical elements embedded in the SCM 712 that are also sensitive to the ultrasound signals, thus offering a system for converting the ultrasound signal to an optical signal. The optical signal is then captured using the detection system 702 with beam 704.

As illustrated in FIG. 7, the system 700 uses a piezoelectric transducer 716 to generate acoustic (ultrasound) waves 710a which are subsequently reflected by a target object of interest 706 generating reflected acoustic pressure waves 710b that propagate to the surface 708. One or more locations on the surface 708 are covered by SCM 712 (for example, a reflective gel containing particles) that is used to detect the arriving pressure (acoustic) waves 710b using an optical ultrasound detection system 702 with beam 704.

The SCM 712 (for example, a reflective gel containing particles) has optical elements suspended in the reflective gel-like medium. The optical elements can be microscopic particles. In one or more embodiments the optical elements suspended in the reflective gel-like medium are nanoparticles. In one or more embodiments the optical elements suspended in the reflective gel-like medium are particles of reflective materials. In one or more embodiments the optical elements suspended in the reflective gel-like medium are aluminum particles. In one or more embodiments the optical elements suspended in the reflective gel-like medium are silver particles. In one or more embodiments the optical elements suspended in the reflective gel-like medium are gold particles. In one or more embodiments the optical elements suspended in the reflective gel-like medium are particles of refractive materials e.g. high index of refraction materials or birefringent materials, or fluorescing materials, or materials which change the polarization of light or can alter some other property of incoming light interacting with it) suspended in the gel so that when the gel is applied to the subject medium the spatial arrangement (e.g. position, displacement, orientation, group organization, etc) and/or physical property and/or optical property of the optical elements are changed by a pressure wave (e.g. sound or ultrasound waves) from the subject medium which in turn produces a corresponding change in the optical response of the composition to an interrogating light (e.g. laser or LED source operating at a suitable single or multiple wavelengths).

Figure 8:
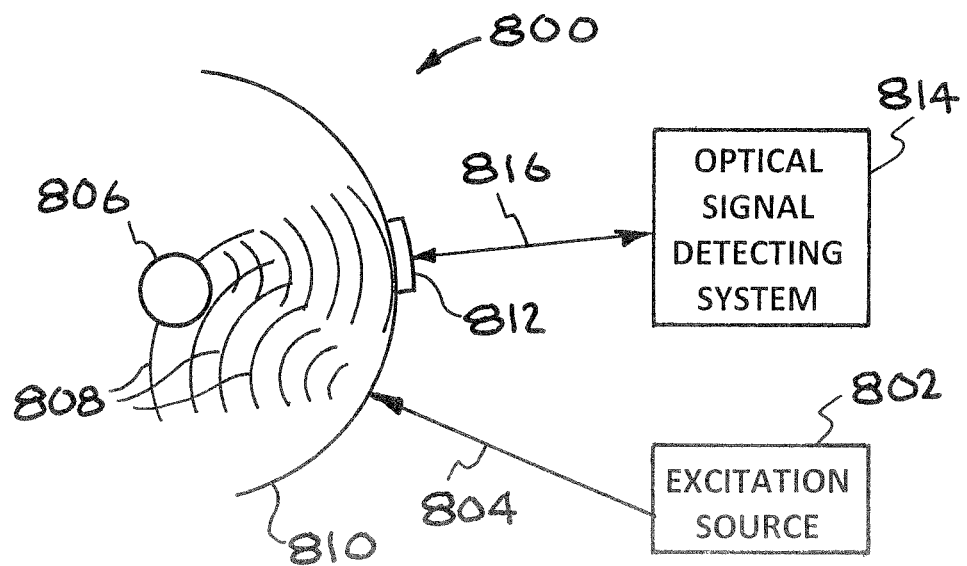
FIG. 8 illustrates a system of the present invention where the pressure waves are generated on the surface by an energy source depositing energy on the surface that causes the generation of the pressure waves.

Referring now to FIG. 8, a non-contact, all optical system for detecting ultrasound is shown where the pressure waves are generated on the surface by an energy source depositing energy on the surface that causes the generation of the pressure waves. The system is designated generally by the reference numeral 800. This can be for example a microwave or optical source that is absorbed by the surface to generate the pressure wave as part of the energy relaxation process. The reflected signal is detected in one or multiple locations using the noncontact method described herein. This method is also a noncontact method but utilizes an external energy source to generate the pressure waves on the surface.

As shown in FIG. 8, a non-contact, all optical system 800 for detecting ultrasound is illustrated where the sound waves 808 are injected in to the material by an energy source 802 depositing energy on the surface 810 that causes the generation of the pressure waves 808. The pressure waves 808 reach a target object of interest 806 and are reflected. The reflected signal 808 from the target object of interest 806 (such as a cyst or a tumor) is detected in one or multiple locations using the noncontact system described herein. One or more locations on the surface 810 are covered by SCM 812 (for example, a reflective gel containing particles) that is used to detect the arriving pressure (acoustic) waves 808 using the optical ultrasound detection system 814. The SCM 812 (for example, a reflective gel containing particles) has optical elements suspended in the reflective gel-like medium.

The system 800 is based on the conversion of the vibrational motion carried by an ultrasound wave into an optical signal 816 via the use of a signal converting material (SCM) 812 that is applied or positioned on the surface 810. This optical signal 816 can be obtained from the modulation of the light scattered by optical elements embedded in the SCM 812. The optical signal 816 is part of the detection system 814.

Figure 9:
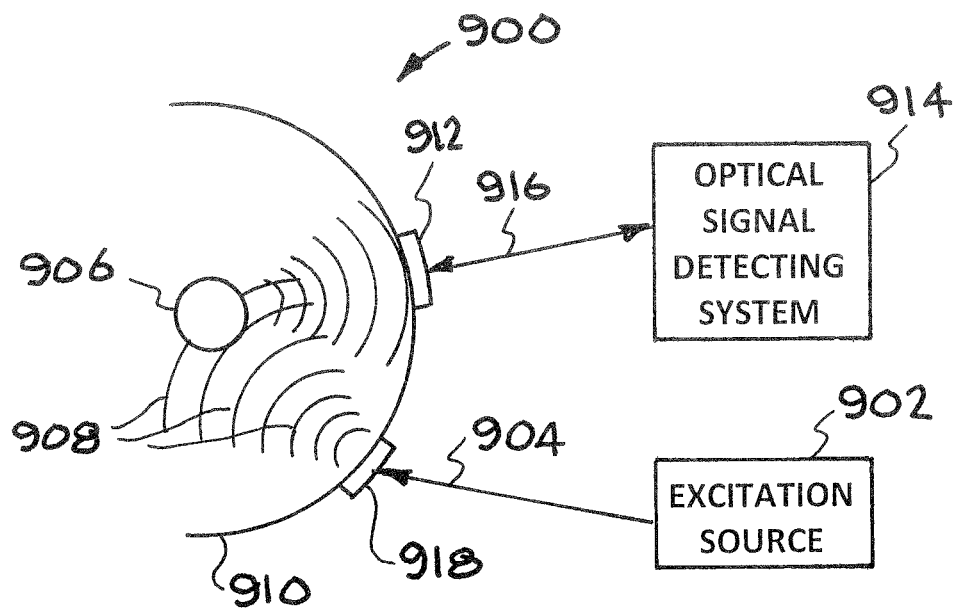
FIG. 9 illustrates a system of the present invention where the pressure waves are generated on the surface by an energy source depositing energy on an energy absorbing material positioned on the surface that causes the generation of the pressure waves.

Referring now to FIG. 9, a non-contact, all optical system for detecting ultrasound is shown where the pressure waves are generated on the surface by an extrinsic absorber positioned in contact with the surface that receives energy from an excitation source depositing energy on the extrinsic absorber that causes the generation of the pressure waves. This can be for example a specially designed material that can also be applied on certain locations on the surface and subsequently excited by an external source such as a light source to generate the pressure waves. The reflected signal is detected in one or multiple locations using the noncontact method described herein. This method is also a noncontact method but utilizes an external medium to generate the pressure waves on the surface.

As shown in FIG. 9, a non-contact, all optical system 900 for detecting ultrasound is illustrated where the sound waves 908 are injected into the material by energy absorbers 918 on the surface 910 that receives energy from an excitation source 902 depositing energy 904 on the energy absorbers 918 that causes the generation of the pressure waves 908. The system is designated generally by the reference numeral 900. The energy absorbers 918 deposits energy on the surface 910 causing the generation of the pressure waves 908. The pressure waves 908 reach a target object of interest 906 and are reflected. The reflected signal 908 from the target object of interest 906 (such as a cyst or a tumor) is detected in one or multiple locations using the noncontact system described herein.

One or more locations on the surface 910 are covered by SCM 912 (for example, a reflective gel containing particles) that is used to detect the arriving pressure (acoustic) waves 908 using the optical ultrasound detection system 914. The SCM 912 (for example, a reflective gel containing particles) has optical elements suspended in the reflective gel-like medium.

The system 900 is based on the conversion of the vibrational motion carried by an ultrasound wave into an optical signal 916 via the use of a signal converting material (SCM) 912 that is applied on the surface 910. This optical signal 916 can be obtained from the modulation of the light scattered by optical elements embedded in the SCM 912. The optical signal 916 is part of the detection system 914.

Figure 10:
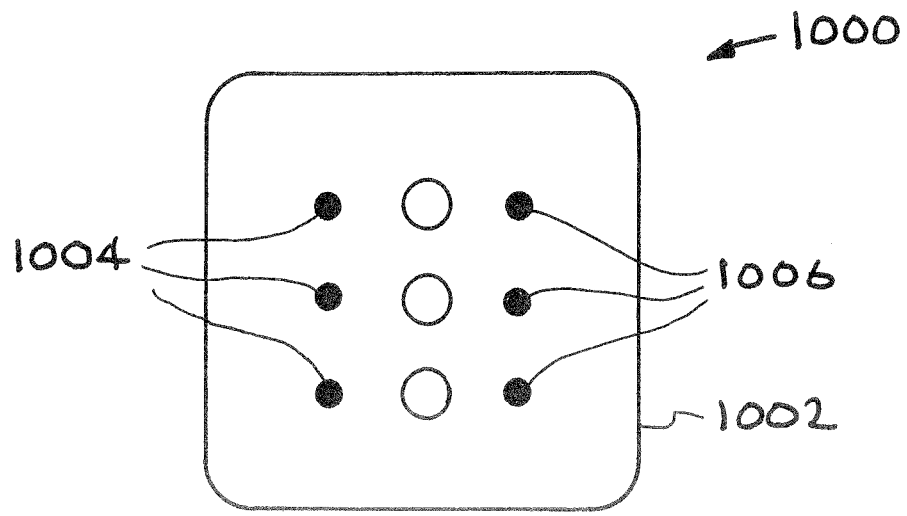
FIG. 10 illustrates one embodiment of a patch of the present invention.

Referring now to FIG. 10, one embodiment of a patch of the present invention is illustrated. The patch is designated generally by the reference numeral 1000. The patch 1000 contains an extrinsic energy absorbing material 1004 for generating pressure waves that are directed to a target object of interest and reflected and a signal converting material 1006 for converting the reflected waves into an optical signal.

The patch 1000 can be applied to one or more locations on the surface and used to generate and subsequently detect pressure waves directed to an absorbing target object of interest. The intrinsic energy absorbing material 1004 is used for generating pressure waves that are directed to an target object of interest (such as a cyst or a tumor) and reflected. The reflected pressure waves are detected using the signal converting material 1006.

The signal converting material 1006 has a spectral structure (such as a multilayer structure) or contains optical elements for conversion of the vibrational motion created by the reflected waves into an optical signal using an optical ultrasound detection system. The optical elements can be microscopic particles, nanoparticles, metal particles, particles of refractive materials, or other signal converting materials. The reflected pressure waves propagate to the surface and the patch 1000 and are detected using a detection system.

The extrinsic energy absorbing material 1004 is used for generating pressure waves that are directed to an target object of interest and reflected. Energy from an external excitation source deposit energy on the extrinsic energy absorbing material 1004 which in turn generates pressure waves. The pressure waves are directed to an absorbing target object of interest and reflected.

Figure 11:
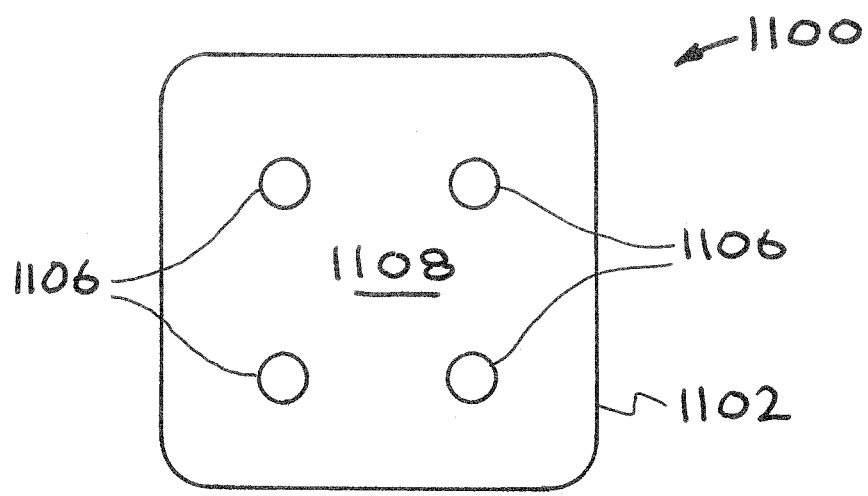
FIG. 11 illustrates another embodiment of a patch of the present invention.

Referring now to FIG. 11, another embodiment of a patch of the present invention is illustrated. The patch is designated generally by the reference numeral 1100. The patch 1100 contains a signal converting material 1106 for converting the pressure waves generated by an energy absorbing target object of interest into an optical signal. The patch 1100 can be applied to one or more locations on the surface and used to detect pressure waves originating from the absorbing target object of interest.

The body 1108 of the patch 1100 is made of a transparent material that allows excitation energy to pass through the patch. In operation, one or more wavelengths from an excitation light source (such as a laser) deposits energy on a light absorbing target object of interest which subsequently generates acoustic pressure waves that propagate to the surface and are detected using the signal converting material 1106 on the patch. Since the body 1108 of the patch 1100 is transparent the excitation energy passes through the patch 1100.

Figure 12:
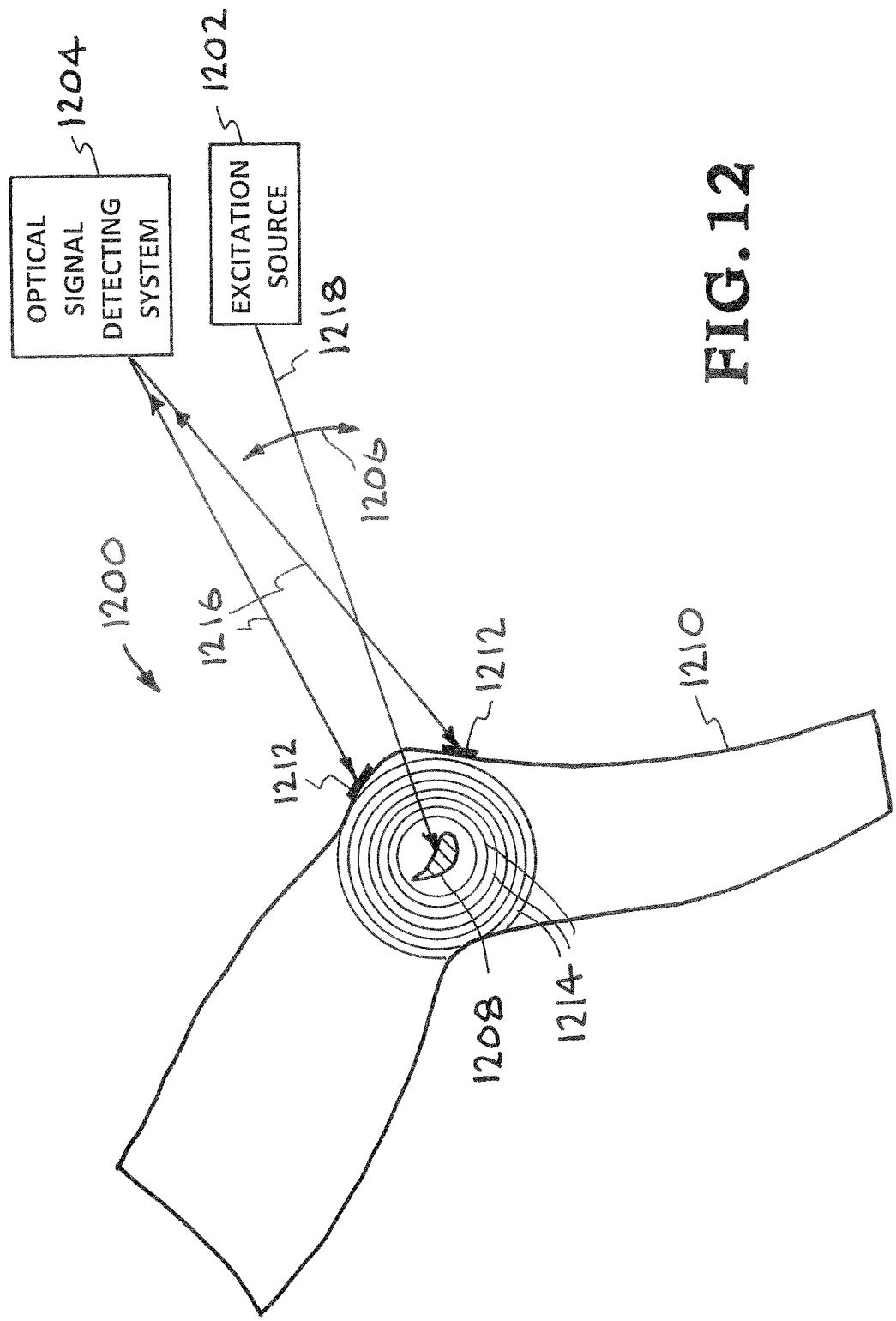
FIG. 12 shows one embodiment of a non-contact, all optical system for detecting ultrasound and obtaining information regarding a knee structure, possible knee injury or condition.

Referring now to FIG. 12 a non-contact, all optical system for detecting ultrasound and obtaining information regarding a possible knee injury or condition is shown. Such arrangement will be suitable for implementation of the teaching of this invention in a human knee or other joint critical for enabling human movement. The detection is based in the generation of the pressure waves by an excitation source or by recording the reflected pressure waves from internal structures after generation of the pressure waves on the surface.

Referring again to FIG. 12, a system that illustrates a non-contact, all optical system to detect ultrasound and obtain information regarding a possible knee injury or condition is shown. The system is designated generally by the reference numeral 1200. The system 1200 provides an all-optical approach and system arrangement suitable for the detection of ultrasound waves reaching the surface 1210. The system is based on the conversion of the vibrational motion carried by an ultrasound wave into an optical signal via the use of a specially designed impedance matching signal converting material (IMSCM) that is applied on the surface. This optical signal can be obtained from the modulation of the light scattered by optical elements embedded in the IMSCM that are also sensitive to the ultrasound signals, thus offering a system for converting the ultrasound signal to an optical signal. The optical signal can then be captured using an appropriate detection system and can be employed without need to be in contact with the surface.

As illustrated in FIG. 12, the system 1200 employs one or more wavelengths 1218 from an excitation source 1202 (such as a laser) used to deposit energy on a light absorbing target object of interest 1208 which subsequently generates acoustic pressure waves 1214 that propagate to the surface 1210. One or more locations on the surface 1210 are covered by an IMSCM 1212 (for example, a reflective gel containing particles) that is used to detect the arriving pressure (acoustic) waves 1214 using an optical signal capturing system 1204.

Figure 13:
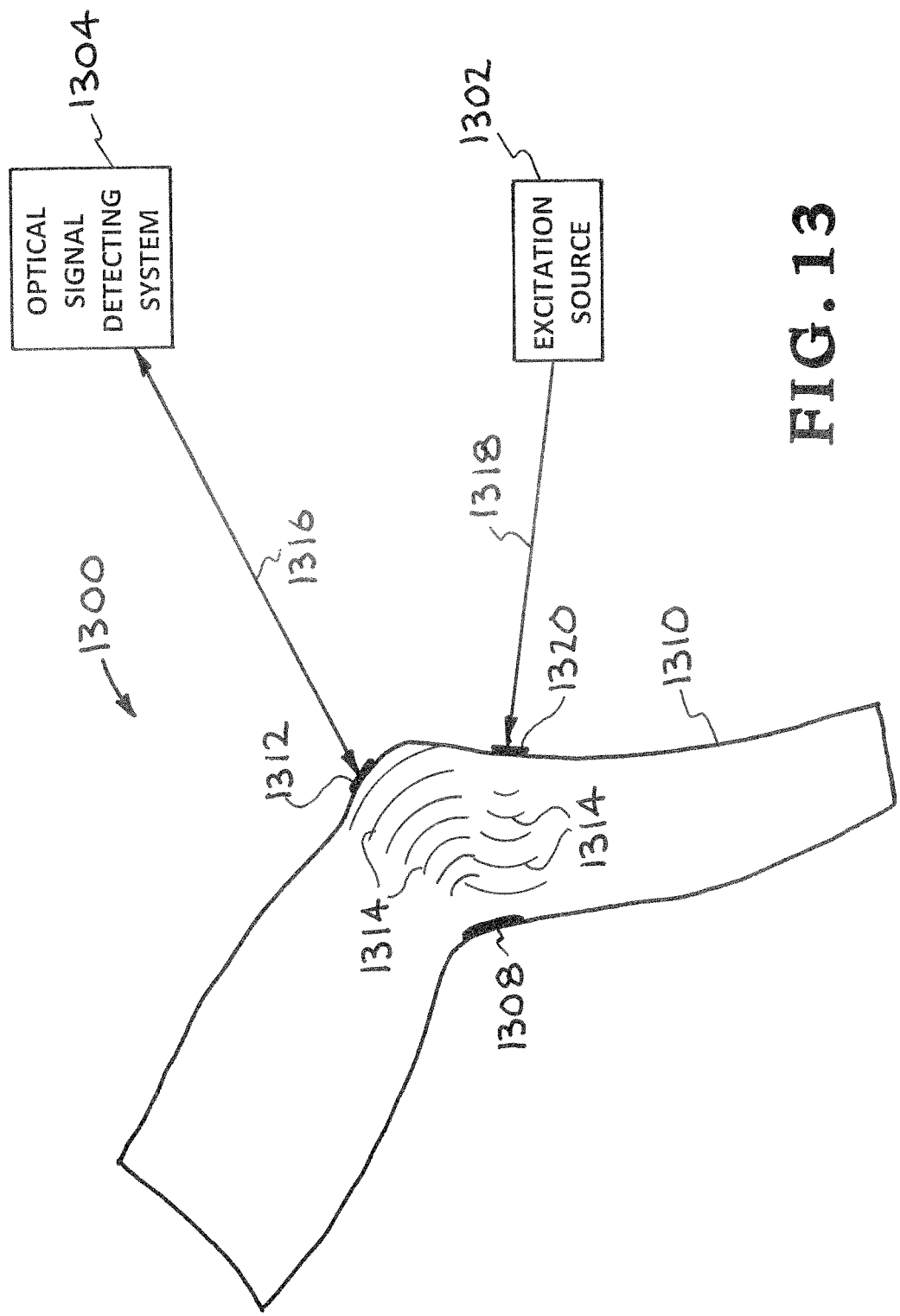
FIG. 13 shows another embodiment of a non-contact, all optical system for detecting ultrasound and obtaining information regarding a knee structure, possible knee injury or condition.

Referring now to FIG. 13 another embodiment of a non-contact, all optical system for detecting ultrasound and obtaining information regarding a possible knee injury or condition is shown or knee anatomical information such as the distance of certain knee structure from the surface. The system is designated generally by the reference numeral 1300. The system 1300 provides an all-optical approach and system arrangement suitable for the generation of pressure waves 1314 and the detection of the reflected pressure waves 1314 reaching the surface 1310. The pressure waves 1314 are generated on the surface 1310 by an extrinsic absorber 1320 located on the surface that receives energy 1318 from an excitation source 1320 depositing energy on the extrinsic absorber 1320 that causes the generation of the pressure waves 1314.

The reflected pressure waves 1314 by an object of interest 1308 are detected using the optical signal capturing system 1304. The reflected pressure waves 1314 are detected using the signal converting material (SCM) 1312. One or more locations 1312 on the surface 1310 contain a patch or reflective gel 1312 that is used to detect the arriving pressure (acoustic) waves 1314 using the optical signal capturing system 1304. The patch or reflective gel 1312 provides a signal converting material (SCM) containing optical elements or specialized structure to provide conversion of the acoustic signal 1314 into optical signal 1316.

Figure 14:
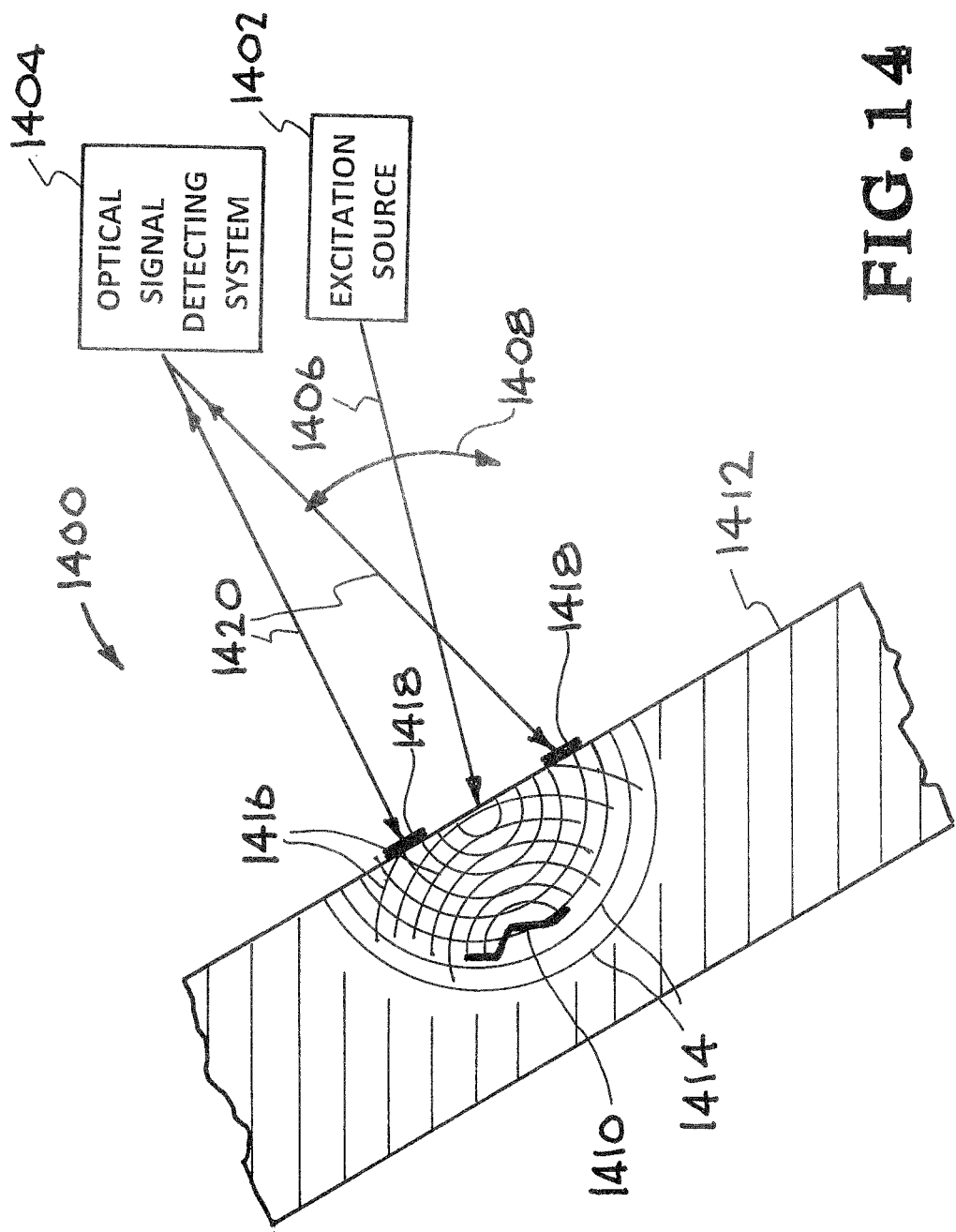
FIG. 14 illustrates a non-contact, all optical non-destructive testing system for detecting defects in an object.

Referring now to FIG. 14 a non-contact, all optical non-destructive testing system for detecting defects in an object is shown. The system is designated generally by the reference numeral 1400. A defect or defective region 1410 is detected by the system 1400. An excitation source 1402 with beam 1406 is used to scan and locate the defect 1410.

The system 1400 employs one or more wavelengths or frequencies from the excitation source 1406 used to deposit energy on the defect 1410 which subsequently generates acoustic pressure waves 1414 that propagate to the surface 1412. One or more locations on the surface 1412 are covered by an SCM 1418 (for example, a reflective gel containing particles) that is used to detect the arriving pressure (acoustic) waves 1414 using an optical ultrasound detection system 1404.

The SCM 1418 (for example, a reflective gel containing particles) has optical elements suspended in the reflective gel-like medium. The optical elements can be microscopic particles. In one or more embodiments the optical elements suspended in the reflective gel-like medium are nanoparticles. In one or more embodiments the optical elements suspended in the reflective gel-like medium are particles of reflective materials. In one or more embodiments the optical elements suspended in the reflective gel-like medium are aluminum particles. In one or more embodiments the optical elements suspended in the reflective gel-like medium are silver particles. In one or more embodiments the optical elements suspended in the reflective gel-like medium are gold particles. In one or more embodiments the optical elements suspended in the reflective gel-like medium are particles of refractive materials e.g. high index of refraction materials or birefringent materials, or fluorescing materials, or materials which change the polarization of light or can alter some other property of incoming light interacting with it) suspended in the gel so that when the gel is applied to the subject medium the spatial arrangement (e.g. position, displacement, orientation, group organization, etc) and/or physical property and/or optical property of the optical elements are changed by a pressure wave (e.g. sound or ultrasound waves) from the subject medium which in turn produces a corresponding change in the optical response of the composition to an interrogating light (e.g. laser or LED source operating at a suitable single or multiple wavelengths).

Figure 15:
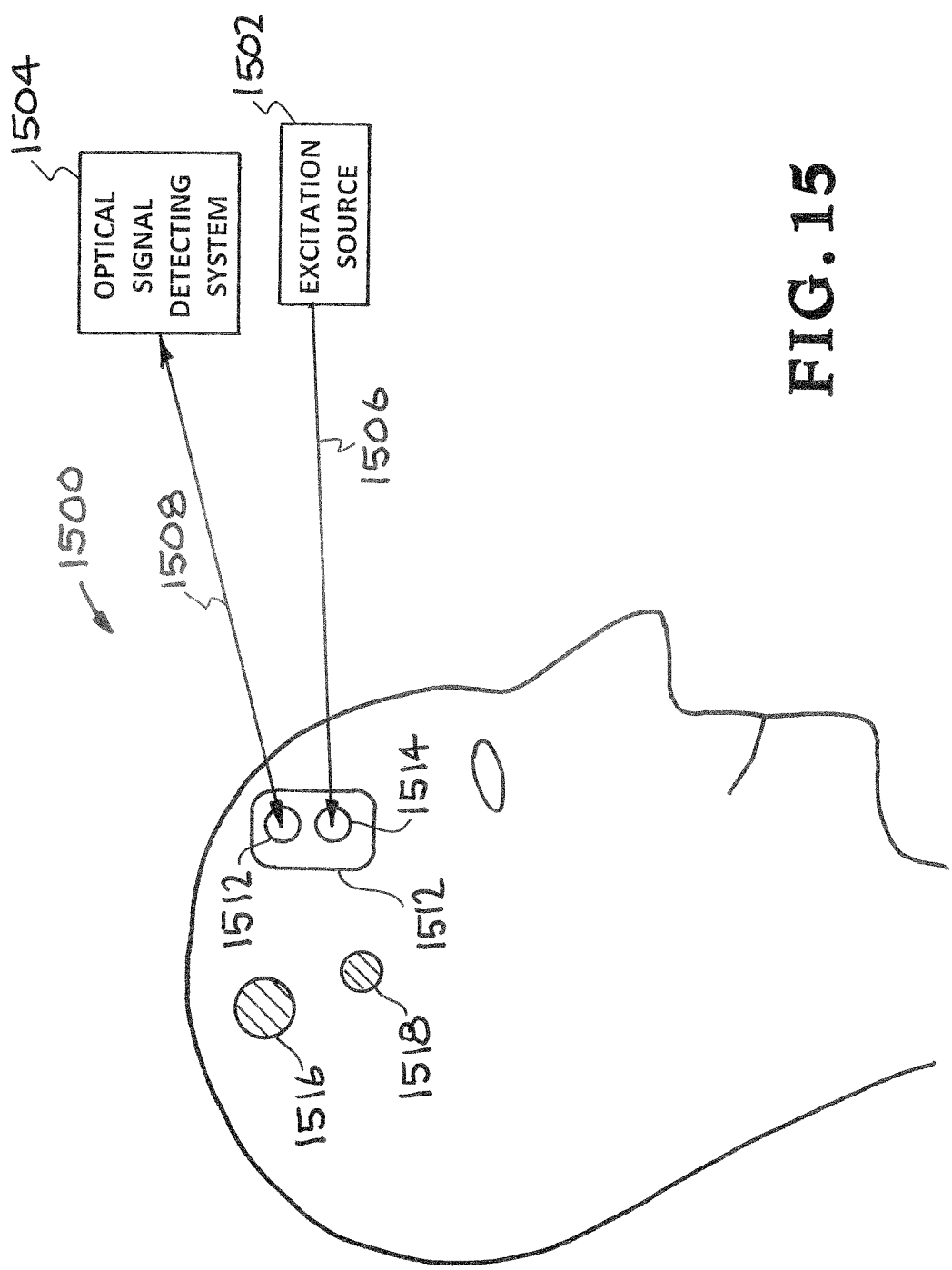
FIG. 15 illustrates another embodiment of a non-contact, all optical system for detecting ultrasound and obtaining information regarding a possible head injury or condition.

Referring now to FIG. 15, another embodiment of a non-contact, all optical system for detecting ultrasound and obtaining information regarding a possible head injury or condition is shown. FIG. 15 is a simplified representation of a patient's head that has suffered a head injury and possible internal head injury resulting, for example, in hematomas 1516 and 1518. The system illustrated in FIG. 15 is designated generally by the reference numeral 1500.

In various medical applications, ultra-sound is used to carry out diagnostic information about such possible internal head injuries such as hematomas 1516 and 1518. In the system 1500 an excitation source 1502 is used to direct the beam 1506 to patch 1510 located on the patient's head. The patch 1510 contains an extrinsic energy absorbing material 1514. The beam 1506 is directed onto the extrinsic energy absorbing material 1514 causing the intrinsic energy absorbing material 1514 to vibrate and generate pressure waves in the tissue of the patient's head. The pressure waves are directed to the hematomas 1516 and 1518 and the pressure waves are reflected from the hematomas 1516 and 1518. The pressure waves reflected from hematomas 1516 and 1518 are received by the signal converting material 1512 on patch 1510 causing the signal converting material 1512 to vibrate. The optical signal detecting system 1504 detects vibration of the signal converting material 1512 using the optical signal 1508.

The body of the patch 1510 is made of a transparent material that allows excitation energy to pass through the patch 1510. This allows the system to be used in an alternative mode. In the alternative mode one or more wavelengths from the excitation source 1502 deposits energy on the hematomas 1516 and 1518 which subsequently generate pressure waves that propagate through the patient's tissue to the surface and are detected by the optical signal detecting system 1504 that detects vibration of the signal converting material 1512 using the optical signal 1508. Since the body 1108 of the patch 1100 is transparent the excitation energy beam 1506 can pass through the patch 1510.

The signal converting material 1512 that used for converting the pressure waves reflected from hematomas 1516 and 1518 can be microscopic particles, nanoparticles, metal particles, particles of refractive materials, or other signal converting materials. The excitation source 1502 may involve one or more wavelengths so that functional information about the hematomas 1516 and 1518 can be obtained. For example, the excitation source 1502 can contain wavelengths that can help assess the content of the hematomas 1516 and 1518 in oxyhemoglobin, deoxyhemoglobin and methemoglobin. The amount of absorption at each wavelength will be directly related to the strength of the pressure waves generated. In turn, this will lead to a corresponding modulation of the signal recorded by the optical signal detecting system 1504. This strength can be deconvoluted in to functional information using established methods.

Figure 16:
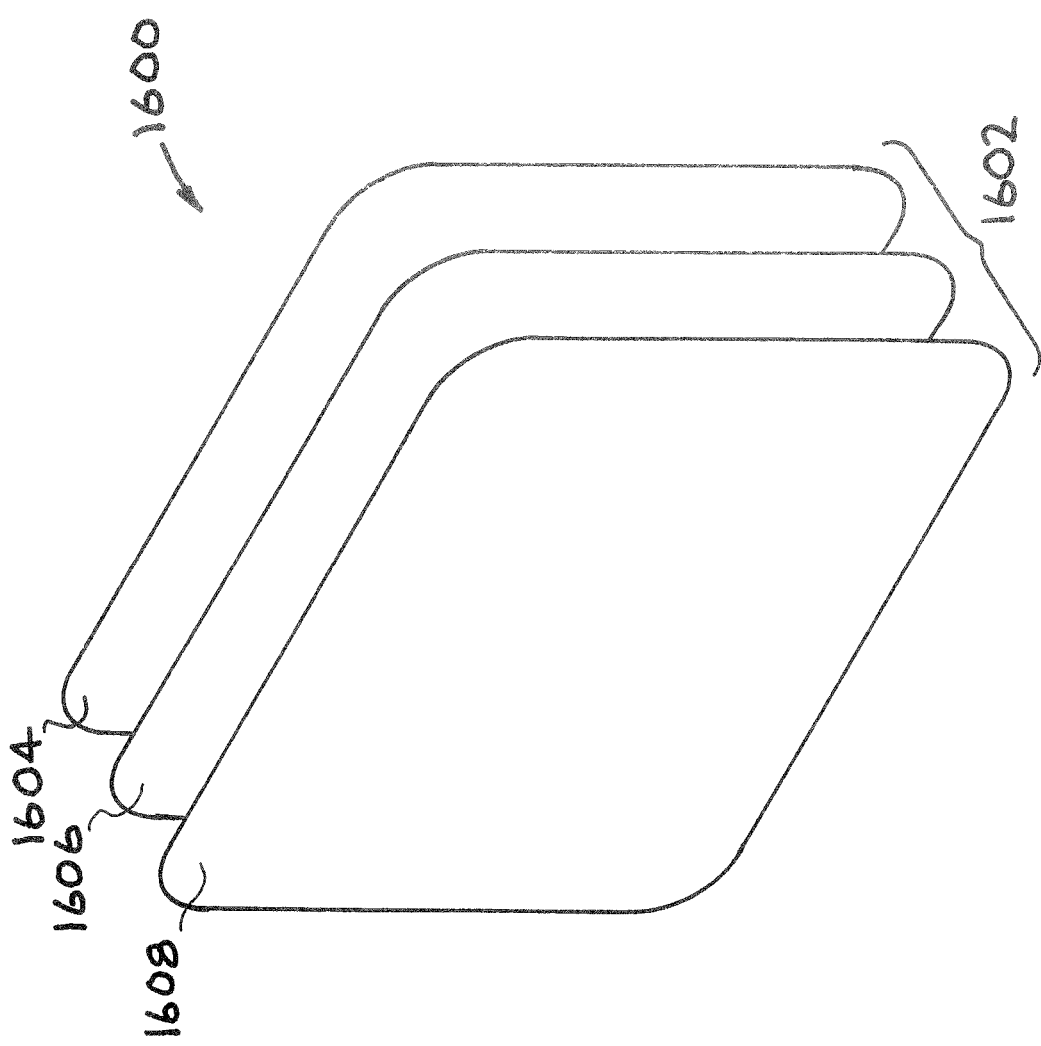
FIG. 16 illustrates another embodiment of a patch of the present invention.

Referring to FIG. 16 another embodiment of a patch of the present invention is illustrated. The patch is designated generally by the reference numeral 1600. The patch 1600 can be applied to one or more locations on the surface and used to detect pressure waves reflected from an absorbing target object of interest. The reflected pressure waves are detected using the patch 1600.

The patch 1600 has a body 1602. The body 1602 has a specially designed multilayer structure. As shown in FIG. 16 the body 1602 of patch 1600 has layers 1604, 1606, and 1608. The body 1602 of patch 1600 can have more layers than layers 1604, 1606, and 1608. The layers 1604, 1606, and 1608 are made of plastic material differing indexes of refraction. The layers 1604, 1606, and 1608 of plastic material with differing indexes of refraction detect the pressure waves reflected from the absorbing target object of interest.

The arriving pressure waves cause vibration of the surface and the multilayer structure 1602, the thickness of the layers 1604, 1606, and 1608 are modified. This in turn causes a change in the interaction of the multilayer structure 1602 with the incoming light which is used to detect the presence and strength of the surface pressure waves. For example, the spectrum of the scattered light under broadband illumination or the intensity of the scattered light at a selected monochromatic illumination will be modulated by the arriving pressure waves.

The present invention provides a medical system for obtaining information about a target organ or entity of a patient through the surface of the patient's tissue, including a signal converting material connected to the surface of the patient's tissue; a unit that directs energy to the target organ or entity of the patient thereby depositing energy on the target organ or entity of the patient, wherein the target organ or entity of the patient subsequently generates pressure waves that propagate to the surface of the patient's tissue and the signal converting material, wherein the pressure waves create modification in the signal converting material; and an optical detection system that senses the modifications in the signal converting material and obtains the information about the target organ or entity of the patient. The present invention also provides a method of obtaining information about a target organ or entity of a patient through the surface of the patient's tissue, including attaching a signal converting material to the surface of the patient's tissue; directing energy to the target organ or entity thereby depositing energy on the target organ or entity, wherein the target organ or entity subsequently generates pressure waves that propagate to the surface of the patient's tissue and the signal converting material, wherein the pressure waves create modifications in the signal converting material; and detecting the modifications in the signal converting material with an optical detection system thereby obtaining information about the target organ or entity of the patient. The present invention also provides a method of obtaining information about an energy absorbing target within an entity having a surface, including attaching a signal converting material to the surface; directing energy to the energy absorbing target thereby depositing energy on the energy absorbing target, wherein the energy absorbing target subsequently generates pressure waves that propagate to the surface of the entity and the signal converting material, wherein the pressure waves create modifications in the signal converting material; and detecting the modifications in the signal converting material with an optical detection system thereby obtaining information about the energy absorbing target.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of obtaining information about a target organ or entity of a patient through the surface of the patient's tissue and through the patient's tissue wherein the patient's tissue has impedance, comprising the steps of:
   providing a laser that produces a laser beam having light that contains energy;
   directing said laser beam directly onto the surface of the patient's tissue and through the patient's tissue to the target organ or entity depositing said energy on the target organ or entity producing pressure waves that propagate from the target organ or entity of the patient through the patient's tissue to the surface of the patient's tissue;
   providing an impedance matching signal converting material cream containing optical elements that scatter light,
   wherein said impedance matching signal converting material cream provides impedance matching with the impedance of the patient's tissue, and
   wherein said impedance matching signal converting material cream enables said optical elements to interact with said pressure waves providing displacement of said optical elements;
   applying said impedance matching signal converting material cream containing optical elements that scatter light to the surface of the patient's tissue wherein said optical elements are particles of reflective materials;
   providing displacement of said optical elements by said energy deposited on the target organ or entity producing said pressure waves that propagate through the patient's tissue to the surface of the patient's tissue and are transferred to said optical elements thereby providing displacement of said optical elements;
   providing an optical detection system laser that produces an interrogating laser light beam; and
   using said interrogating laser light beam for detecting said displacement of said optical elements to provide the information about the target organ or entity of the patient.

2. An apparatus for providing information about a target organ or entity of a patient through the surface of the patient's tissue and through the patient's tissue wherein the patient's tissue has impedance, comprising:
   an excitation laser;
   an excitation laser beam produced by said excitation laser;
   an impedance matching signal converting material cream that is impedance matched with the impedance of the patient's tissue wherein said impedance matching signal converting material cream is connected to the surface of the patient's tissue;
   optical elements in said impedance matching signal converting material cream that scatter light wherein said optical elements are particles of reflective materials and wherein said impedance matching signal converting material cream is impedance matched with said particles of reflective materials;
   a system that directs said excitation laser beam directly onto the surface of the patient's tissue and through the patient's tissue to the target organ or entity which produces pressure waves that propagate from the target organ or entity through the patient's tissue to the surface of the patient's tissue and create vibrations of the surface of the patient's tissue that propagate to said impedance matching signal converting material cream with said optical elements that scatter light and cause displacement of said optical elements;
   an optical detection system laser;
   an interrogating laser light beam produced by said optical detection system laser that is directed to said optical elements and reflected from said optical elements; and
   an optical signal detection system that receives said reflected interrogating laser light beam and detects said displacement of said optical elements and provides information about the target organ or entity of the patient.

3. An apparatus for obtaining information about a tumor of a patient through the surface of the patient's tissue and through the patient's tissue wherein the patient's tissue has impedance, comprising:
   an excitation laser;
   an excitation laser beam produced by said laser;
   an impedance matching signal converting material cream that is impedance matched with the impedance of the patient's tissue wherein said impedance matching signal converting material cream is connected to the surface of the patient's tissue;
   optical elements in said impedance matching signal converting material cream that scatter light wherein said optical elements are particles of reflective materials;
   a system that directs said excitation laser beam directly onto the surface of the patient's tissue and through the patient's tissue to the tumor of the patient which produces pressure waves that propagate from the tumor of the patient through the patient's tissue to the surface of the patient's tissue and creates vibrations of the surface of the patient's tissue and causes displacement of said optical elements;
   an optical detection system;
   an interrogating laser beam produced by said optical detection system laser that is directed to said optical elements and reflected from said optical elements; and an optical signal detection system that receives said reflected interrogating laser beam and detects said displacement of said optical elements thereby detecting the information about the tumor of the patient.

4. A method of obtaining information about a tumor within a patient's tissue beneath the patient's tissue surface wherein the patient's tissue has impedance, comprising the steps of:

providing a laser that produces a laser beam having light that contains energy;

directing said laser beam directly onto the patient's tissue surface and through the patient's tissue depositing said energy on the tumor generating pressure waves from the tumor that propagate through the patient's tissue to the patient's tissue surface;

providing an impedance matching signal converting material cream containing optical elements that scatter light wherein said optical elements are particles of reflective materials;

designing said impedance matching signal converting material cream containing optical elements to provide impedance matching with the impedance of patient's tissue, attaching said impedance matching signal converting material cream to the patient's tissue surface;

providing displacement of said optical elements by said pressure waves from the tumor propagating through the patient's tissue to the patient's tissue surface thereby displacing said optical elements that scatter light;

providing an optical detection system laser that produces an interrogating laser light beam; and using said interrogating laser light beam of said optical detection system laser to detect said displacement of said optical elements to obtain the information about the tumor.

* * * * *